United States Patent
Koch

(10) Patent No.: US 8,149,003 B2
(45) Date of Patent: Apr. 3, 2012

(54) METHOD AND DEVICE FOR DETERMINING THE HUMIDITY CONTENT OF AN INSULATION OF A TRANSFORMER

(75) Inventor: Maik Koch, Lindau (DE)

(73) Assignee: Omicron Electronics GmbH, Klaus (AT)

( * ) Notice: Subject to any disclaimer, the term of this patent is extended or adjusted under 35 U.S.C. 154(b) by 833 days.

(21) Appl. No.: 12/187,702

(22) Filed: Aug. 7, 2008

(65) Prior Publication Data
US 2009/0051374 A1    Feb. 26, 2009

(30) Foreign Application Priority Data
Aug. 17, 2007 (EP) .................... 07016221

(51) Int. Cl.
*G01R 27/08* (2006.01)
*G01R 31/06* (2006.01)
*H01H 31/12* (2006.01)
(52) U.S. Cl. .............. 324/694; 324/547; 324/551
(58) Field of Classification Search .............. 324/694, 324/547, 551
See application file for complete search history.

(56) References Cited

U.S. PATENT DOCUMENTS
| | | | | |
|---|---|---|---|---|
| 5,534,853 | A * | 7/1996 | Pioch .................... | 340/646 |
| 6,870,374 | B2 * | 3/2005 | Perkins et al. .......... | 324/551 |

FOREIGN PATENT DOCUMENTS
| | | |
|---|---|---|
| DE | 2059669 | 6/1972 |
| DE | 10013001 | 9/2001 |
| DE | 10135915 | 3/2003 |
| DE | 10314592 | 10/2003 |
| DE | 69726139 | 8/2004 |

OTHER PUBLICATIONS
Cigre Task Force, Gubanski, Boss, Csepes, Der Houhanessian, Filippini, Guuinic, Gafvert, Karius, Lapworth, Urbani, Werelius, Zaengl; "Dielectric Response Methods For Diagnostics of Power Transformers"; DEIS, IEEE Electrical Insulation Magazine; 2003, pp. 12-18; XP002464320.

Dervos, C.T., Paraskevas, C.D., Skafidas, P., Vassiliou, P.; "Dielectric Characterization of Power Transformer Oils as a Diagnostic Life Prediction Method"; DEIS, vol. 21, No. 1, Feb. 2005, pp. 11-19, XP002464321.

Tapan K. Saha, Prithwiraj Purkait; "Investigation of An Expert System for the Condition Assessment of Transformer Insulation Based on Dielectric Response Measurements"; IEEE Transactions on Power Delivery, vol. 19, No. 3, Jul. 2004, pp. 1127-1134, XP002464322.

Walter S Zaengl; "Applications of Dielectric Spectroscopy in Time and Frequency Domain for HV Power Equipment"; DEIS, vol. 19, No. 6, Dec. 2003, pp. 9-22, XP002464323.

(Continued)

*Primary Examiner* — Amy He
(74) *Attorney, Agent, or Firm* — Wood, Herron & Evans, LLP

(57) ABSTRACT

A method and a device for determining a humidity content of an insulation of a transformer, the insulation having a liquid. At least one dielectric property of the insulation is measured, an uncorrected humidity content of the insulation and a conductivity of a liquid which is included in the insulation is derived from a model of the insulation, said model being chosen depending on the measured dielectric property of the insulation, and the humidity content of the insulation is corrected by means of the conductivity.

20 Claims, 3 Drawing Sheets

OTHER PUBLICATIONS

Tapan K. Saha; "Review of Time-Domain Polarization Measurements for Assessing Insulation Condition in Aged Transformers"; IEEE Transactions on Power Delivery, vol. 18, No. 4, Oct. 2003, pp. 1293-1301, XP002464324.

Gafvert, Adeen, Tapper, Ghasemi, Jonsson; "Dielectric Spectroscopy in Time and Frequency Domain Applied to Diagnostics of Power Transformers"; Proc. of the 6th Intl. Conf. on Properties and Applications of Dielectric Materials, Jun. 26, 2000, pp. 825-830, XP002464325.

Dipl.-Ing. Maik Koch, Prof. Dr.-Ing. Stefan Tenbohlen; "Der Bubble-Effekt and das Risiko eines Dielektrischen Fehlers in Leistungstransformatoren"; ETG Diagnostik Elektrotechnischer Betriebsmittel, Sep. 19-20, 2006 Kassel. (including English Abstract).

Dipl.-Ing. Maik Koch, Prof. Dr.-Ing. Stefan Tenbohlen; "Ein Neues Verfahren zur Online-Feuchtemessung in Leistungstransformatoren"; ETG Diagnostik Elektrotechnischer Betriebsmittel, Sep. 19-20, 2006, Kassal. (including English Abstract).

Dipl.-Ing. Maik Koch, Prof, Dr.-Ing. Stefan Tenbohlen; "Einflussgroben and Zuverlassigkeit bei Dielektrischen Diagnosemethoden zur Bestimmung des Feuchtegehalts". (including English Abstract).

* cited by examiner

METHOD AND DEVICE FOR DETERMINING THE HUMIDITY CONTENT OF AN INSULATION OF A TRANSFORMER

The present application claims the priority of European Patent Application No. EP 07 016 221.9 filed Aug. 17, 2007 under 35 U.S.C. §119. The disclosure of that priority application is hereby fully incorporated by reference herein.

BACKGROUND OF THE INVENTION

This invention concerns a method for determining a humidity content of an insulation of a transformer, and a device of corresponding form.

Humidity, in particular in the case of oil-paper insulations of power transformers, reduces their electrical strength, makes them age faster and can result in formation of gas bubbles in the insulation. The humidity content of the insulation is understood to mean a percentage water content in the insulation. Knowledge of the humidity content in solid parts of the insulation, e.g. paper or pressboard, is of great importance for safe operation of power transformers. For measuring the humidity content in the solid parts of the insulation, dielectric measurement methods, which derive the humidity content from one or more dielectric properties of the insulation, have been developed. This measurement can be done in the time or frequency domain, the results being measured magnitudes or dielectric properties such as polarization and depolarization currents, the dissipation factor tangens delta, the dielectric constant. From these measured magnitudes, by comparison with a model, the humidity content in the solid part of the insulation or the solid insulation can be calculated.

It is problematical that the dielectric properties of the insulation can be affected not only by water, but also by other conductive aging products, so that additional humidity can be simulated by these aging products. Therefore, the measured or analyzed humidity content or water content is typically too high compared with the actual humidity content, in particular in the case of very aged transformers with a relatively highly conductive insulation system. This wrong diagnosis because the humidity content is wrongly too highly measured can result in unnecessary maintenance actions, e.g. drying.

SUMMARY OF THE INVENTION

According to an embodiment of the invention, a method for determining a humidity content of an insulation of a transformer, the insulation including a liquid, particularly oil, is provided. The method according to this embodiment includes the following steps which allow to more precisely determine the humidity content of the insulation:
- determining or measuring one or more dielectric properties of the insulation
- deriving a provisional humidity content and a conductivity of the liquid from a model of the insulation, depending on the measured dielectric property
- correcting the provisional humidity content using the conductivity, to determine the humidity content of the insulation.

Conductive aging products may be, in particular, dissociated acids, which are both dissolved in the liquid (particularly oil) and carried in the solid part of the insulation (particularly paper). Thermodynamic exchange processes result in an equilibrium of the distribution of the aging products between the liquid and the non-liquid or solid parts of the insulation. An embodiment of the invention comprises deducing the aging-affected properties of the solid parts of the insulation from the aging-affected properties of the liquid. For this purpose, the dielectric effects of the aging products in the insulation are determined by modelling, the results of which are the uncorrected humidity content and the conductivity of the liquid. Through the conductivity, it is possible to deduce the proportion of aging products in the solid part of the insulation. Expressed otherwise, through knowledge of the conductive aging products in the liquid, the conductive aging products in the solid part of the insulation and thus the effects of these aging products in the solid part of the insulation are determined. It is thus possible to compensate for the effects of the conductive aging products in the solid part of the insulation, so that the water which is simulated by the conductivity of the aging products in the solid part of the insulation is taken into account in the determination of the humidity content of the insulation, so that the determination of the humidity content is more precise than in the case of methods which are known according to the prior art.

By precise determination of the humidity content of the insulation, unnecessary maintenance actions, e.g. drying, and therefore unnecessary stoppage times of transformers and finally costs, can be avoided.

Compensation of the dielectric properties of the aging products in the solid part of the insulation preferably takes place through a correction formula. This correction formula is determined, for instance, by measuring multiple insulations, which are impregnated with liquid of different conductivity, in particular oil, in the laboratory. Here it must be taken into account that by impregnation with, for instance, oil of different conductivity, the apparent humidity content of the insulation is also changed. Through these laboratory measurements, therefore, a relationship between a real humidity content of the insulation and a modelled humidity content of the invention depending on the conductivity is obtained.

Then, according to an embodiment of the invention, using this relationship or this correction formula, for each humidity content which is given and determined from the model, using the conductivity, the real humidity content can be determined, and/or the humidity content which is determined from the model can be corrected correspondingly.

In an embodiment of the invention, the insulation is an oil-paper insulation, so that the liquid is oil.

In the case of this embodiment, the dielectric effects of the aging products in oil are determined through the modelling, giving an oil conductivity as the result. This oil conductivity now makes it possible to draw a conclusion about the proportion of aging products in the paper which simulate water by their conductivity. Through the knowledge of the conductive aging products in the oil, the effect of the conductive aging products in the paper or pressboard is then compensated for.

According to an embodiment of the invention, a model of the insulation is determined such that at least one measured dielectric property of the insulation agrees better with this model than with other models. For this purpose, parameters of the model, in particular the humidity content of the insulation and the conductivity of the liquid, are optimized so that the at least one dielectric property which is derived from the model agrees optimally with the measured at least one dielectric property. In other words, the model of the insulation with the best agreement regarding the at least one measured dielectric property of the insulation is determined. Then, from this model which is determined in this way, the provisional humidity content and the conductivity (to correct the humidity content) can be derived.

By choosing the model by which the at least one measured dielectric property of the insulation, e.g. polarization and depolarization currents of the insulation, the dissipation factor tangens delta or the dielectric constant of the insulation, are best given, from this model, the provisional or uncorrected humidity content and the conductivity can best be derived, so that then, in a further step, by means of the conductivity, the correct humidity content of the insulation can best be determined.

According to an embodiment of the invention, the model takes account of a temperature of the insulation, corresponding essentially to a temperature of the transformer.

In a further embodiment according to the invention, the model includes an X-Y model for multi-layer insulations, in this case in particular oil-paper insulations. This can be, for instance, the X-Y model which is known from U. Gafvert, G. Frimpong and J. Fuhr: "Modelling of dielectric measurements on power transformers", Proc. 37th Session "Large High Voltage Electric Systems" (CIGRE), paper 103, Paris, France, 1998.

The method according to the invention may preferably be carried out to determine a humidity content of a power transformer or high voltage transformer. A power transformer is understood to be a transformer which is used to transmit electric power via, for instance, high voltage lines. In this case, high voltage is a voltage of 1000 V or more. Accordingly, in a high voltage transformer, at least the primary or the secondary side has a high voltage. However, other applications of the invention, of course, are possible as well.

According to an embodiment of the invention, compensation for the effects of the conductive aging products in the solid part of the insulation usually takes place software-based, so that, for instance, it is unnecessary to produce multiple comparison data sets for differently aged insulations.

According to yet another embodiment of the invention, a device for determining a humidity content of an insulation of a transformer is provided, the insulation having a liquid. The device includes a measuring device to measure a dielectric property of the insulation, and a processing unit. The processing unit is capable of deriving a provisional humidity content of the insulation and an oil conductivity of the liquid from a previously created model of the insulation, and correcting the provisional humidity content of the insulation using the conductivity, to determine the humidity content of the insulation.

The advantages of the device according to this embodiment for determining the humidity content of the insulation correspond essentially to the above-mentioned advantages of the method for determining the humidity content of the insulation, for which reason they are not repeated here.

With this embodiment, in particular, the humidity content of the insulation of a transformer can be precisely determined. However, this invention is of course not restricted to this preferred application field, but this invention can also be used to determine the humidity content of other objects which comprise a liquid and a solid part, and where thermodynamic exchange processes ensure an even distribution of aging products between the liquid and the solid part. An example of such an object is an insulation which is used with other electrical engineering high voltage devices such as high voltage switches.

BRIEF DESCRIPTION OF THE DRAWINGS

Below, this invention is explained in more detail by an embodiment, with reference to the attached drawings.

DETAILED DESCRIPTION OF THE INVENTION

Figure 1:
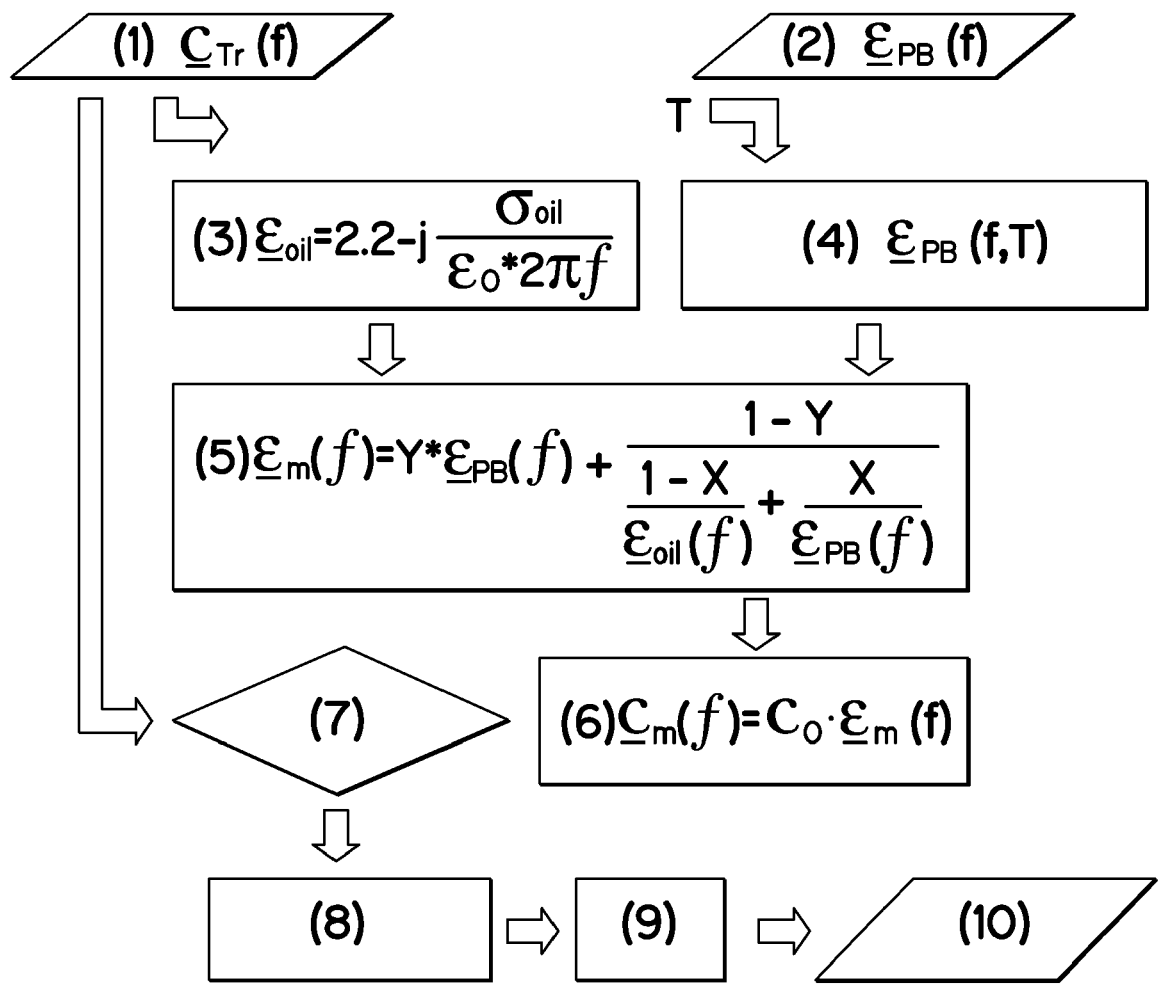
FIG. 1 shows a flowchart for an embodiment according to the invention of a method for determining a humidity content of an insulation of a transformer.

In Step 1 of FIG. 1, dielectric properties of an insulation of a transformer and the temperature of the insulation are measured depending on a frequency f of a voltage which is applied to the transformer. The dielectric properties of the insulation correspond to the dielectric properties of the transformer, and are dielectric properties which a capacitance of the transformer $C_{Tr}(f)$ also has. These dielectric properties include polarization currents, depolarization currents, the dissipation factor tangens delta and the dielectric constant.

In Step 2, different dielectric responses of pressboard and paper (i.e. of the solid part of the insulation) $\in_{PB}(f)$, depending on the temperature, and on a humidity content of the pressboard and paper, and on the frequency f of the voltage which is applied to the transformer, are provided as a database, as the basis of a model of the insulation.

In Step 3, a formula by which dielectric responses and/or dielectric properties of an insulating oil $\in_{oil}(f)$ can be determined, depending on the conductivity $\sigma_{oil}$ of the oil, the frequency f of the voltage which is applied to the transformer and the permittivity of the vacuum $\in_0$, is introduced into the method.

In Step 5, the dielectric responses of pressboard, paper and oil are combined with each other via a mathematical X-Y model. X represents a proportion of insulating barriers in the insulation, and Y represents a proportion of spacers in the insulation. The X-Y model therefore reflects a ratio of liquid insulation (oil) to solid insulation (pressboard, paper in barriers and spacers). The temperature T of the transformer is taken into account by a Step 4. The result is a dielectric response of the model $\in_m(f)$.

Then, in Step 6, using the geometrical capacitance $C_0$, a model capacitance $C_m(f)$ is calculated.

By a fitting algorithm or optimization algorithm, the parameters humidity content of the pressboard and paper and conductivity $\sigma_{Oil}$ of the oil are optimized so that the dielectric properties of the capacitance of the real transformer $C_{Tr}(f)$ (i.e. the dielectric properties which were measured in Step 1) agree best with the dielectric properties of the modelled capacitance $C_m(f)$ and/or with the dielectric properties of the model. In other words, the model properties of the modelled capacitance $C_m(f)$ are adjusted to the properties of the real transformer by varying the parameters of the model (humidity content and conductivity $\sigma_{oil}$). This is represented schematically in FIG. 1 by a comparison step 7, in which the dielectric properties of the transformer $C_{Tr}(f)$ are compared with those of the model $C_m(f)$. The properties of the optimally fitting model, or of the model which supplies the best agreement with the real transformer, are considered as properties of the real insulation of the transformer.

Then, as the result, the conductivity of the oil $\sigma_{Oil}$ and a still uncorrected water content or humidity content in the pressboard and paper are determined from the model, see Step 8. The humidity content is too high, particularly at high oil conductivities. High oil conductivities occur particularly in the case of greatly aged transformers, so that here the uncorrected humidity content is higher than the real humidity content of the pressboard and paper.

Now, in Step 9, with knowledge of the conductivity of the oil, the effect of conductive aging products in the pressboard and paper is compensated for. The oil conductivity makes it possible to draw a conclusion about the proportion of aging products in the pressboard and paper which simulate water by their conductivity. This conclusion is possible because the paper and pressboard are impregnated with the same oil for which the oil conductivity was determined by the modelling.

Then, in Step 10, the corrected humidity content in the paper and pressboard, i.e. the humidity content of the insulation, and the oil conductivity are output.

The compensation which is carried out in Step 9 is based on a correction formula by which the modelled too high water content is corrected to the correct value. The correction formula is acquired by measurements on paper insulations which are impregnated with differently conductive oil. In other words, the method described above (Steps 1 to 8) is carried out for multiple paper insulations, the oil with which these paper insulations is impregnated, and thus the real humidity content of the paper insulation, being known. From the real humidity content, the uncorrected humidity content which is determined through the model, and the conductivity, the correction formula with which the correct or real humidity content of the insulation is determined, according to the invention, from the uncorrected humidity content (result of Step 8), can be created.

Figure 2:
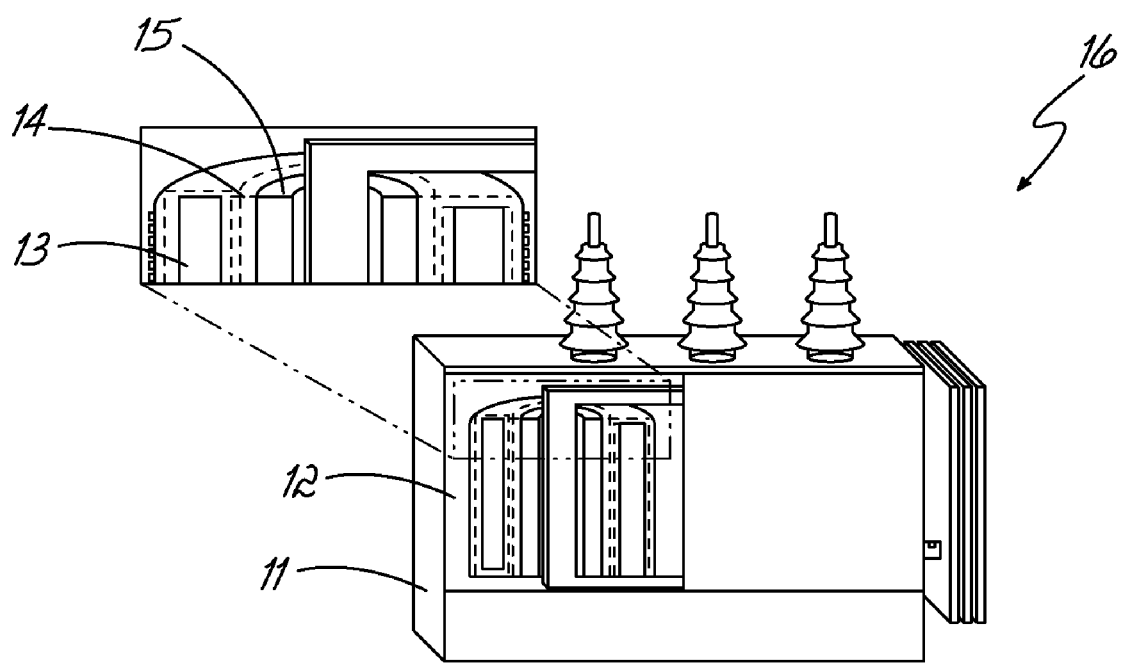
FIG. 2 shows, schematically, a high voltage transformer, with the insulation of which the method according to the invention can be used.

In FIG. 2, an oil-paper-insulated transformer 16 is shown. A tank 11 of the transformer 16 is filled with insulating oil 12. Between a higher voltage winding 13 and a lower voltage winding 15 of the transformer 16 is a solid part 14 of an insulation of the transformer 16. The insulation thus consists of pressboard and paper 14 and the poured-in insulating oil 12. The humidity content of the insulation can be precisely determined by the method discussed above according to an embodiment of the invention.

Figure 3:
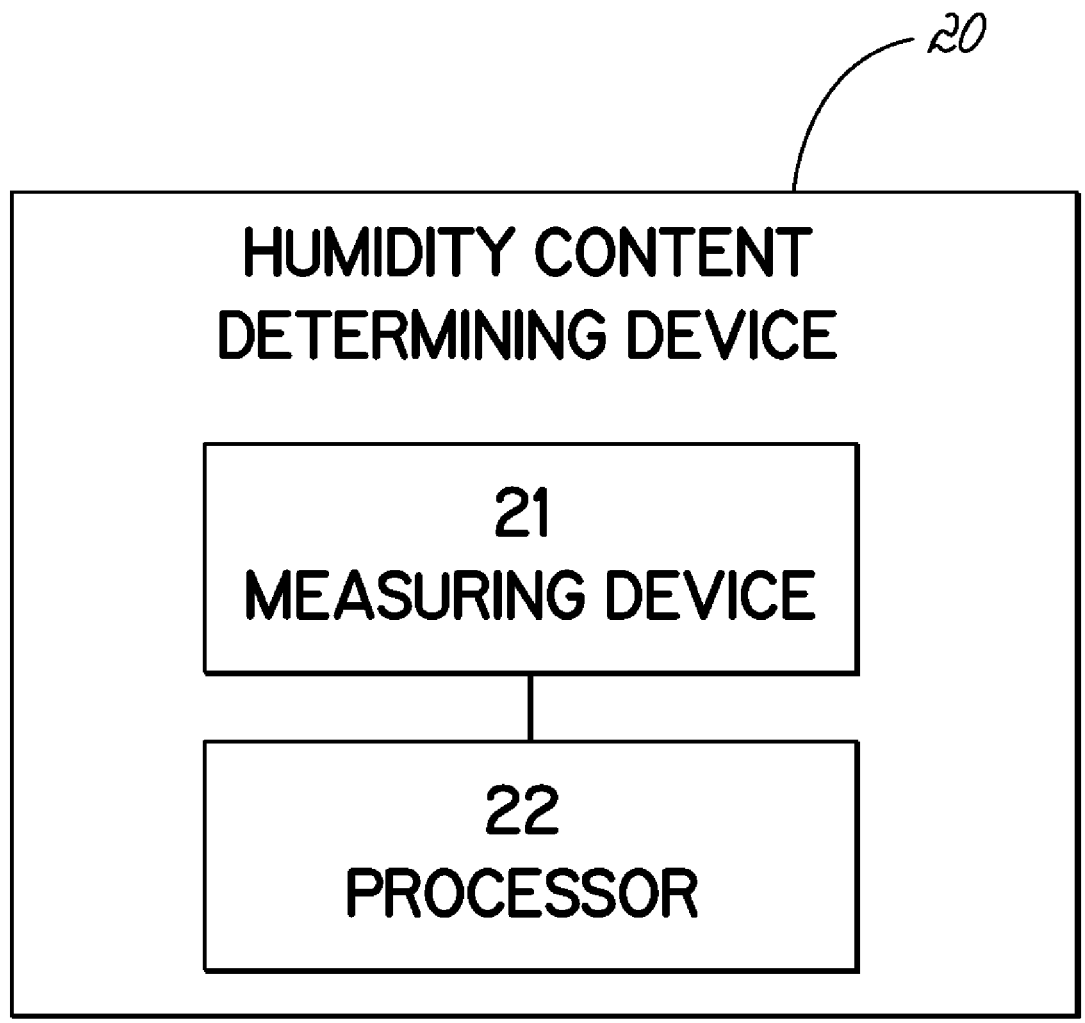
FIG. 3 shows, schematically, a device according to an embodiment of the invention for determining a humidity content of an insulation of a transformer.

In FIG. 3, schematically, a device 20 according to an embodiment of the invention is shown, to determine the humidity content of the insulation 12, 14 of the transformer 16. The device 20 includes a measuring device 21 to measure a temperature T of the transformer and its insulation, and to measure dielectric properties of the dielectric which forms the insulation, and which consists of the insulating oil 12 and the paper and pressboard 14. The device 10 also includes a processor 22, which from the dielectric properties of the insulation 12, 14 and the conductivity of the insulating oil 12, by the method sketched above, calculates the humidity content of the insulation, particularly of the paper and pressboard 14.

What is claimed is:

1. A method for determining a humidity content of an insulation of a transformer, the method comprising the following steps:
    measuring at least one frequency dependent dielectric property of the insulation,
    providing a model of the insulation, said model being chosen depending on the at least one measured dielectric property of the insulation,
    deriving an uncorrected humidity content of the insulation and a conductivity of a liquid which is included in the insulation from said model of the insulation, and
    determining a corrected humidity content of the insulation using a known relationship between a real humidity content of the insulation and the uncorrected humidity content of the insulation in dependence on the conductivity of the liquid.

2. The method according to claim 1, wherein the known relationship between the real humidity content of the insulation and the uncorrected humidity content in dependence on the conductivity is obtained by measurements on insulations which are impregnated with liquids of different conductivity.

3. The method according to claim 1, wherein the insulation is an oil-paper insulation, and wherein the liquid is oil.

4. The method according to claim 1, wherein the step of providing said model of the insulation comprises choosing at least one parameter of the model of the insulation so that the at least one dielectric property of the model is essentially the same as the measured at least one dielectric property.

5. The method according to claim 4, wherein the at least one parameter comprises the humidity content of the insulation and the conductivity of the liquid.

6. The method according to claim 1, wherein the step of providing said model of the insulation comprises providing said model of the insulation such that the model takes account of the temperature of the insulation.

7. The method according to claim 1, wherein the step of providing said model of the insulation comprises creating said model of the insulation by means of an X-Y model for multi-layer insulations.

8. The method according to claim 1, wherein the method is carried out to determine a humidity content of a high voltage transformer.

9. The method according to claim 1, wherein the step of providing said model of the insulation comprises creating automatically said model of the insulation depending on the at least one measured dielectric property of the insulation.

10. A device for determining a humidity content of an insulation of a transformer, comprising:
    a measuring device to measure at least one frequency dependent dielectric property of the insulation, and
    a processing unit, the processing unit being constructed such that the processing unit derives a humidity content of the insulation and a conductivity of a liquid which is included in the insulation from a model which is chosen depending on the at least one measured dielectric property of the insulation, and corrects the humidity content of the insulation by means of the conductivity.

11. The device according to claim 10, wherein the at least one frequency dependent dielectric property of the insulation is measured by measuring the capacitance of the transformer with respect to frequency.

12. A device for determining a humidity content of an insulation of a transformer, comprising:
    a measuring device to measure at least one frequency dependent dielectric property of the insulation, and
    a processing unit, the processing unit being constructed such that the processing unit derives a humidity content of the insulation and a conductivity of a liquid which is included in the insulation from a model which is chosen depending on the at least one measured dielectric property of the insulation, and corrects the humidity content of the insulation by means of the conductivity, wherein the device is constructed to:
    measure at least one frequency dependent dielectric property of the insulation,
    provide a model of the insulation, said model being chosen depending on the at least one measured dielectric property of the insulation,
    derive an uncorrected humidity content of the insulation and a conductivity of a liquid which is included in the insulation from said model of the insulation, and
    determine a corrected humidity content of the insulation using a known relationship between a real humidity content of the insulation and the uncorrected humidity content of the insulation in dependence on the conductivity of the liquid.

13. The device according to claim 12, wherein the known relationship between the real humidity content of the insulation and the uncorrected humidity content in dependence on the conductivity is obtained by measurements on insulations which are impregnated with liquids of different conductivity.

14. The device according to claim 12, wherein the insulation is an oil-paper insulation, and wherein the liquid is oil.

15. The device according to claim 12, wherein providing said model of the insulation comprises choosing at least one parameter of the model of the insulation so that the at least one dielectric property of the model is essentially the same as the measured at least one dielectric property.

16. The device according to claim 15, wherein the at least one parameter comprises the humidity content of the insulation and the conductivity of the liquid.

17. The device according to claim 12, wherein providing said model of the insulation comprises providing said model of the insulation such that the model takes account of the temperature of the insulation.

18. The device according to claim 12, wherein providing said model of the insulation comprises creating said model of the insulation by means of an X-Y model for multi-layer insulations.

19. The device according to claim 12, wherein the corrected humidity content of the insulation is determined for a high voltage transformer.

20. The method according to claim 12, wherein providing said model of the insulation comprises creating automatically said model of the insulation depending on the at least one measured dielectric property of the insulation.

* * * * *